United States Patent [19]

Zellweger

[11] Patent Number: 5,516,529

[45] Date of Patent: May 14, 1996

[54] GRANULATES USEFUL FOR PREPARING EFFERVESCENT PESTICIDE TABLETS

[76] Inventor: Jean-Michel Zellweger, Valentin 60, 1004 Lausanne, Switzerland

[21] Appl. No.: 90,553

[22] Filed: Jul. 12, 1993

Related U.S. Application Data

[63] Continuation of Ser. No. 821,307, Jan. 14, 1992, abandoned, which is a continuation of Ser. No. 506,397, Apr. 6, 1990, abandoned.

[30] Foreign Application Priority Data

Apr. 7, 1989 [CH] Switzerland ............................. 1300/89

[51] Int. Cl.$^6$ ................................. A61K 9/46; A61K 9/16; A01N 25/34; A01N 25/12
[52] U.S. Cl. ........................ 424/466; 424/715; 424/717; 424/489; 424/684; 424/691; 424/724; 424/408; 428/402
[58] Field of Search ..................................... 424/466, 715, 424/717, 489, 499–502; 428/402; 252/7

[56] References Cited

U.S. PATENT DOCUMENTS

| | | | |
|---|---|---|---|
| 3,764,668 | 10/1973 | Higuchi et al. | 424/44 |
| 3,891,756 | 6/1975 | Kasugai et al. | 514/802 |
| 4,076,808 | 2/1978 | Lorenz et al. | 514/114 |
| 4,303,556 | 12/1981 | Llendado | 252/174.14 |
| 4,599,233 | 7/1986 | Misato et al. | 424/127 |
| 4,687,662 | 8/1987 | Schobel | 424/44 |

FOREIGN PATENT DOCUMENTS

| | | |
|---|---|---|
| 0076340 | 4/1983 | European Pat. Off. . |
| 0847370 | 9/1960 | United Kingdom . |
| 1103238 | 2/1968 | United Kingdom . |
| 2016271 | 9/1979 | United Kingdom . |

OTHER PUBLICATIONS

Chemical Abstracts 101/146,146c (1984).
Chemical Abstracts 98/102,733g (1983).
Derwent Abstract No. 70803x/38.
Chemical Abstracts 80/56,317c (1974).
Derwent Abstract No. 83-37122 k/16.
Stephen Brunauer et al., The Journal of the American Chem. Society, vol. IX, pp. 309–319 (1938).

*Primary Examiner*—Edward J. Webman
*Attorney, Agent, or Firm*—Edward McC. Roberts; Marla J. Mathias

[57] ABSTRACT

An effervescent granulate consisting of a solid water-soluble acidic substance, potassium carbonate and/or potassium hydrogen carbonate and one or more water-insoluble substances that are capable of absorbing water, a pesticidal active ingredient concentrate that is in the form of effervescent tablets and contains the effervescent granulate, and the preparation of the effervescent granulate and of the pesticidal active ingredient concentrate are described.

14 Claims, No Drawings

GRANULATES USEFUL FOR PREPARING EFFERVESCENT PESTICIDE TABLETS

This is a continuation of Ser. No. 07/821,307, filed Jan. 14, 1992, now abandoned, which in turn is a continuation of Ser. No. 07/506,397, filed Apr. 6, 1990, now abandoned.

The present invention relates to pesticidal active ingredient concentrates in the form of effervescent tablets that contain a water-insoluble pesticidal active ingredient and disintegrate in water to form a sprayable suspension, to an effervescent granulate suitable for the preparation of those effervescent tablets, and to processes for the preparation of the effervescent granulate and the effervescent tablets.

The preparation of effervescent tablets containing active ingredients having biological activity, such as pharmaceuticals and pesticides, is known. Such effervescent tablets generally contain a disintegrator which generates gas on contact with water. These disintegrators usually consist of a water-soluble acidic substance and an alkali metal or alkaline earth metal carbonate, suitable water-soluble acidic substances being especially polybasic organic acids, such as succinic acid, tartaric acid, adipic acid and citric acid, and suitable carbonates being especially sodium carbonate and sodium hydrogen carbonate. Most commonly used are disintegrators based on sodium carbonate and/or sodium hydrogen carbonate and citric acid.

The preparation of effervescent tablets containing a water-insoluble active ingredient gives rise to particular problems which are due especially to the fact that the water-insoluble constituents of the tablet, such as the active ingredient and insoluble adjuvants, have to be ground very finely in order to ensure that, when the tablet has disintegrated in water, the particles have good suspension properties and a homogeneous suspension is formed. However, since the flow properties of a powder mixture deteriorate as the particle size decreases, problems frequently occur when such finely ground mixtures are formed into tablets, and these problems increase further as the content of active ingredient increases. Such problems are, for example, lamination and capping, poor separation of the tablets from the mould and uneven filling of the moulds. Further problems are caused by the water-insoluble active ingredient, especially when it has pronounced hydrophobic properties. It has been found that finely ground hydrophobic active ingredients render inactive the disintegrator, which usually consists of sodium carbonate and an acidic substance, by accumulating on its surface. This effect is more pronounced the smaller the particle size of the active ingredient and the higher the active ingredient content in the tablet. This results in an increase in the disintegration time of the tablet that is not acceptable in practice.

It is not possible to solve this problem by simply replacing sodium carbonate with potassium carbonate, which is more active as an effervescent component, since potassium carbonate is very difficult to handle on account of its strongly hygroscopic properties. Potassium carbonate has a pronounced tendency to absorb moisture from its surroundings, which leads to the premature disintegration both of effervescent mixtures and of effervescent tablets. Nor is the desired aim achieved by rendering the acid inactive by reaction with potassium carbonate at the crystal surface in the presence of a defined amount of a polar solvent, such as water, methanol and ethanol or mixtures of those solvents, as is described in EP-A-0 076 340 for mixtures of sodium carbonate and citric acid. Because of these difficulties, potassium carbonate has hitherto rarely been used in the industrial manufacture of effervescent tablets.

The problem on which the present invention is based is to provide an effervescent granulate which is based on potassium carbonate and a solid water-soluble acidic substance and is suitable for the preparation of effervescent tablets that contain a water-insoluble pesticidal active ingredient and disintegrate rapidly in water to form a sprayable suspension.

It has been found that the sensitivity to moisture of mixtures of solid acidic substances with potassium carbonate can be reduced to an extraordinarily great degree if there are added to those mixtures from 5 to 20% by weight of a finely divided water-insoluble substance that is capable of binding water.

The present invention therefore relates to an effervescent granulate which contains, in addition to a solid water-soluble acidic substance and potassium carbonate and/or potassium hydrogen carbonate, from 5 to 20% by weight of a finely divided water-insoluble substance that is capable of binding water.

Suitable solid water-soluble acidic substances are generally water-soluble polybasic acids or their acid salts. Examples of suitable solid acidic substances are sodium hydrogen sulfate, potassium hydrogen sulfate, sodium dihydrogen phosphate, polybasic carboxylic acids or the acid salts of those polybasic carboxylic acids. Preferred solid water-soluble acidic substances are polybasic carboxylic acids, such as succinic acid, tartaric acid, adipic acid and citric acid. Citric acid is especially preferred.

The ratio of potassium carbonate and/or potassium hydrogen carbonate to solid water-soluble acidic substance can be varied within wide limits. Both the potassium carbonate and/or potassium hydrogen carbonate and the solid water-soluble acidic substance may be present in a stoichiometric excess. For example, the effervescent granulate according to the invention may contain from 0.5 to 1.5 equivalents of solid water-soluble acidic substance per equivalent of potassium carbonate and/or potassium hydrogen carbonate. Preferably, the effervescent granulate according to the invention contains from 0.8 to 1.2 equivalents of solid water-soluble acidic substance per equivalent of potassium carbonate and/or potassium hydrogen carbonate. Especially preferably, the effervescent granulate according to the invention contains from 1.0 to 1.2 equivalents of solid water-soluble acidic substance per equivalent of potassium carbonate and/or potassium hydrogen carbonate.

Suitable water-insoluble substances capable of binding water are, for example, highly dispersed silicic acids, amorphous and crystalline aluminosilicates, aluminium oxide and clay minerals, or mixtures of such substances. Highly dispersed silicic acids are especially suitable as water-insoluble substances capable of binding water.

Precipitated or pyrogenic silicic acid is suitable as the highly dispersed silicic acid. Especially suitable is precipitated or pyrogenic silicic acid having an agglomerate size of from 5 to 50 μm and a surface area, measured according to BET (see J. Amer. Chem. Soc. (1938), 60, page 309) of from 200 to 500 m$^2$/g.

Suitable amorphous aluminosilicates are especially the substances that have become known under the name "Silica Alumina". They can be prepared by adding an aqueous solution of an aluminium salt, for example aluminium sulfate, to an aqueous solution of a silicate, for example sodium silicate, filtering the resulting precipitate, washing with water and calcining. A further preparation process consists in precipitating silica gel from an aqueous solution of sodium silicate by the addition of sulfuric acid and, after a certain ageing period, adding aluminium sulfate and ammonia to the silica gel, the pH value being kept in the weakly acid range. The precipitate is then filtered, washed and calcined. With regard to the preparation of amorphous aluminosilicates, reference is also made to U.S. Pat. Nos. 2,283,172 and 2,283,173. More detailed information on the structure of "Silica Alumina" will be found in Ind. Eng. Chem. 41, (1949), 2564–2573. Amorphous aluminosilicates that can be used according to the invention contain from 5 to 30% by weight of $Al_2O_3$ and from 70 to 95% by weight of $SiO_2$. They have an inner surface area, measured according to BET, of from 50 to 800 $m^2/g$ and a pore volume of from 0.1 to 3 $cm^3/g$. The particle size may be from 5 to 50 µm, preferably from 8 to 25 µm.

Suitable crystalline aluminosilicates are especially natural and synthetically produced zeolites ground to a particle size of from 5 to 50 µm, preferably from 8 to 25 µm.

Suitable aluminium oxides are especially aluminas, as used for column chromatography. Suitable clay minerals are especially bentonite, montmorillonite and bauxite. The insoluble substance capable of binding water advantageously contains less than 5% by weight of water. Preferably, the insoluble substance capable of binding water contains less than 3% by weight of water.

The effervescent granulate according to the invention preferably contains from 5 to 20% by weight, especially preferably from 5 to 10% by weight, of water-insoluble substance capable of binding water.

The effervescent granulate according to the invention is prepared by adding from 5 to 20 parts by weight of a finely divided water-insoluble substance capable of binding water to from 80 to 95 parts by weight of a mixture comprising a solid water-soluble acidic substance and potassium carbonate and/or potassium hydrogen carbonate, stirring the resulting mixture with from 25 to 50 parts by weight of a $C_1$–$C_6$alkanol to form a paste, and then removing the alkanol in vacuo and granulating the residue.

Of the $C_1$–$C_6$alkanols, $C_3$–$C_4$alkanols are preferred. Especially preferred alkanols are isopropanol and isobutanol. The alkanols are preferably used in amounts of from 30 to 40 parts by weight. The removal of the alkanol may be effected under pressures in the range of from 0.02 to 0.1 bar. Preferably, the removal of the alkanol is effected under pressures in the range of from 0.02 to 0.05 bar. The removal of the alkanol may be effected in the temperature range of from 40° to 80° C. The alkanol is preferably removed at a temperature of from 50° to 70° C.

For granulation, the residue obtained after removal of the alkanol is ground and passed through a sieve having a mesh size of from 0.5 to 1 mm. The granulate so obtained can be used for the preparation of effervescent tablets without further preliminary treatment. However, it can also be stored in closed containers for many months without decomposition occurring. The effervescent granulate according to the invention is, however, also relatively stable in air, which considerably facilitates handling. For example, it can be stored at room temperature in contact with air having a relative humidity of up to 40% for several hours without any appreciable change taking place. For the preparation of effervescent tablets, the effervescent granulate according to the invention is mixed with a finely ground mixture of the active ingredient and the other adjuvants, such as surface-active agents, fillers and binders, lubricants, which facilitate removal of the tablet from the mould, and flow regulators, to give a mixture (feedstock) that can be formed directly into tablets, and that mixture is formed into tablets using customary tablet-forming devices. By means of the effervescent granulate according to the invention it is possible to prepare effervescent tablets which, while having good mechanical strength, disintegrate very rapidly in water to form a sprayable suspension. The particular advantage of the effervescent granulate according to the invention is that rapid disintegration of the effervescent tablet in water is ensured even if the effervescent tablet contains a high concentration of strongly hydrophobic active ingredients.

The effervescent tablets prepared using the effervescent granulate according to the invention represent a pesticidal active ingredient concentrate that is easy to prepare and handle, and the present invention relates also to that concentrate.

The present invention therefore relates also to a pesticidal active ingredient concentrate in the form of effervescent tablets, which disintegrates in water to form a sprayable suspension and consists essentially of a water-insoluble active ingredient, surface-active agents, fillers and binders, flow regulators and a disintegrator, which concentrate contains the disintegrator in the form of an effervescent granulate comprising potassium carbonate and/or potassium hydrogen carbonate, a solid water-soluble acidic substance and a water-insoluble substance that is capable of binding water.

In accordance with the present invention, this active ingredient concentrate in the form of effervescent tablets is prepared by a) adding from 5 to 20 parts by weight of a water-insoluble substance capable of binding water to from 80 to 95 parts by weight of a mixture comprising a solid water-soluble acidic substance and potassium carbonate and/or potassium hydrogen carbonate, stirring the resulting mixture with from 25 to 50 parts by weight of a $C_1$–$C_6$alkanol to form a paste, and then removing the alkanol in vacuo and granulating the residue, b) mixing together the finely ground active ingredient and the other adjuvants, such as surface-active agents, flow regulators, lubricants, fillers and binders, and c) mixing together the granulate prepared under a) and the powder mixture prepared under b) and forming the resulting feedstock into tablets.

The tablets can be formed in customary tablet-forming devices. Tablets having good mechanical strength can be produced using pressures of from 500 to 800 $kg/cm^2$.

The preparation of the effervescent granulate according to section a) has already been described in detail above. Reference can therefore be made to the above comments for details of the preparation of the effervescent granulate according to section a).

For the preparation of the powder mixture according to section b), the following procedure is advantageously adopted: Firstly, the active ingredient and other water-insoluble constituents are ground to a particle size in the range of from 3 to 50 µm, preferably from 5 to 15 µm, and then the remaining constituents, such as surface-active agents, flow regulators, lubricants, fillers and binders, are mixed in. With active ingredients that tend to form lumps on grinding, an anti-caking agent, for example highly dispersed silicic acid, is advantageously added. However, the amount of anti-caking agent used must be such that it represents less than 2% by weight, preferably less than 1% by weight, of the powder mixture prepared under b).

In process step c) the pre-mixtures prepared under a) and b) are mixed together in a conventional mixer. The resulting feedstock is suitable for direct use in the formation of tablets. However, because of the good stability of the effervescent granulate, the mixture can be stored in closed containers for a virtually unlimited period of time. The quality of the mixture is not adversely affected even by many hours' contact with air having a relative humidity of up to 40%.

Generally suitable as active ingredients that may be contained in the effervescent tablet according to the invention are herbicides, plant-growth-regulators, fungicides and insecticides that are insoluble in water. Especially suitable active ingredients are those which are highly active and which are used at application rates of less than 500 g/ha, preferably less than 150 g/ha. The effervescent tablets according to the invention can contain from 2 to 50% by weight of active ingredient. Preferably, the effervescent tablets according to the invention contain from 5 to 25% by weight of active ingredient, especially preferably from 7.5 to 15% by weight of active ingredient.

The effervescent tablet according to the invention may also contain liquid active ingredients if they are adsorbed on a porous carrier, for example silica gel and highly dispersed silicic acid. In that case, however, the maximum content of active ingredient in the tablet is 5% by weight, since higher contents of active ingredient would require larger amounts of highly dispersed silicic acid as carrier, which would impair the mechanical strength of the tablet.

The following may be mentioned as classes of suitable active ingredients and suitable individual compounds:

Phenoxyphenoxy- and pyridyloxyphenoxy-propionic acid derivatives having herbicidal activity, for example the n-butyl ester of 2-[4-(5-chloropyrid-2-yloxy)-phenoxy]-propionic acid (fluazifop-butyl) and the propargyl ester of 2-[4-(5-chloro-3-fluoropyrid-2-yloxy)-phenoxy]-propionic acid;

Sulfonylureas having herbicidal activity, for example N-[2-(2-chloroethoxy)-phenyl]-N'-(4-methoxy-6-methyl-1,3, 5-triazin-2-yl)-urea, N-[2-(2-methoxyethoxy)-phenyl-N'-(4,6-dimethoxy-1,3,5-triazin-2-yl)-urea and N-(2-methoxycarbonylphenyl)-N'-(4,6-bis-difluoromethoxypyrimidin-2-yl)-urea;

1,3-Cyclohexanedione derivatives having plant-growth-regulating activity, for example 2-cyclopropylcarbonyl-5-ethoxycarbonyl-1,3-cyclohexanedione;

Benzoylurea derivatives having insecticidal activity, such as N-difluorobenzoyl-N'-(4-chlorophenyl)-urea (diflubenzuron), N-(2,6-difluorobenzoyl)-N'-[2,5-dichloro-4-(2,2,3, 5,5,5-hexafluoropropoxy)-phenyl]-urea, and also urea derivatives having insecticidal activity, such as N-(2,6-diisopropylphenyl-4-phenoxyphenyl)-N'-tert.-butylurea;

Pyrethroids having insecticidal activity, such as α-cyano-3-phenoxybenzyl-3-(2-chloro-3,3,3-trifluoropropenyl)-2, 2-dimethylcyclopropanecarboxylate (cyhalothrin), especially the (S)(Z)-(1R)-cis and (R)(Z)-(1S)-cis isomers, α-cyano-3-phenoxybenzyl-3-(2,2-dichlorovinyl)-2,2-dimethylcyclopropanecarboxylate (cypermethrin), especially the S-1R-cis and R-1S-cis isomers, deltamethrin;

Melamine derivatives having insecticidal activity, for example N-cyclopropyl-1,3,5-triazine-2,4,6-triamine (cyromazine);

5-pyrimidinemethanol derivatives having fungicidal activity, such as α-(2-chlorophenyl)-α-(4'-chlorophenyl)-5-pyrimidinemethanol (fenarimol), α-(2-chlorophenyl)-α-(4'-fluorophenyl)-5-pyrimidine (nuarimol);

1-substituted 1H-1,2,4-triazole derivatives, such as 1-(4-chlorophenoxy)-3,3-dimethyl-1-(1H-1,2,4-triazol-1-yl)-2-butanone (triadimefon), 1-(4-chlorophenoxy)-3,3-dimethyl-1(1H-1,2,4-triazol-1-yl)-butan-2-ol (triadimenol), 1-[2-(2,4-dichlorophenyl)-pentyl]-1H-1,2,4-triazole (penconazole), 1-[2-(2,4-dichlorophenyl)-4-propyl-1,3-dioxolan-2-ylmethyl]-1H-1,2,4-triazole (propiconazole); and also urea derivatives having fungicidal activity, for example 1-(2-cyano-2-methoximinoacetyl)-3-ethylurea (cymoxanil), and piperazine derivatives having fungicidal activity, for example 1,1'-piperazine-1,4-diyldi-[N-(2,2,2-trichloroethyl)-formamide](triforine).

As further suitable active ingredients there may be mentioned the fungicides that have become known under the common names diniconazole, hexaconazole, cyproconazole, tebuconazole, flusilazole, myclobutanil and pyrifenox.

As surface-active agents there may be used non-ionic and ionic substances. Suitable non-ionic surface-active agents are especially ethoxylated alcohols, fatty acids and phenols, as well as polyethylene glycols and ethylene oxide/propylene oxide block polymers, ethoxylated phenols and ethylene oxide/propylene oxide block polymers, depending on the consistency and degree of polymerisation, also acting as lubricants which facilitate the removal of the tablets from the mould during tablet formation. Suitable ionic surface-active agents are especially anionic substances, such as sodium laurylsulfate, sodium dodecylbenzenesulfonate, polymeric sulfonic acids, such as lignosulfonate, condensation products of naphthalenesulfonic acid with formaldehyde and condensation products of naphthalenesulfonic acid and phenolsulfonic acid with formaldehyde, these substances being used especially in the form of their sodium salts. Also suitable for use as anionic surface-active agents are alkylphenol polyglycol ether phosphates and sulfates and also the alkali metal and amine salts thereof, such as sodium, potassium, triethylamine, triethanolamine and diethanolamine salts. Preferred surface-active agents are alkylphenol polyglycol ether phosphates and their alkali metal and amine salts, as well as sodium lignosulfonate and condensation products of aromatic sulfonic acids with formaldehyde. The effervescent tablet according to the invention can contain from 2 to 20% by weight, especially from 5 to 12% by weight, of surface-active agents.

In addition to the above-mentioned surface-active agents that can be used as lubricants, such as sodium laurylsulfate and polyglycol ether, there are suitable as lubricants especially stearic acid and the salts thereof, such as calcium, magnesium and aluminium stearate, and also talcum (magnesium silicate) and sodium benzoate. The effervescent tablet according to the invention can contain from 0.5 to 4% by weight and especially from 0.5 to 2% by weight of lubricants. Preferred lubricants are stearic acid and its magnesium, calcium and aluminium salts, the amount of which should not exceed 2% by weight because of their pronounced water-repelling action. Sodium benzoate is also an especially suitable water-soluble lubricant.

As suitable flow regulators there may be mentioned, in addition to highly dispersed silicic acid (pyrogenic and precipitated silicic acid), amorphous aluminosilicate (Silica Alumina), crystalline aluminosilicates, especially zeolites, and also alumina and clays, such as bentonite, montmorillonite and bauxite. The content of flow regulators may be from 0 to 15% by weight. The use of flow regulators depends to a considerable extent on the properties of the active ingredient. The use of flow regulators is recommended especially in the case of active ingredients that tend to form lumps when ground to a suitable particle size of from 3 to 50 μm. Especially suitable flow regulators are precipitated and pyrogenic silicic acids. Since those substances have, at the same time, a pronounced anti-caking effect, the content thereof in the powder mixture prepared according to process step b), which contains the active ingredient, should not exceed 2% by weight, since a higher content of flow regulators has an adverse effect on the mechanical strength of the effervescent tablet, especially when highly dispersed silicic acid is used. For that reason, the powder mixture prepared according to process step b) preferably contains less than 1% by weight of highly dispersed silicic acid.

Suitable fillers and binders are, for example, polyglycol ethers having a molecular weight of over 6000, linear or cross-linked polyvinylpyrrolidone, lactose, starch, dextrin, maltodextrin and cellulose derivatives. The effervescent tablet according to the invention can contain from 10 to 50% by weight, preferably from 20 to 40% by weight, of fillers and binders. An especially suitable binder is spray-dried lactose, which is commercially available under the name Tablettose® EP 6113.

The effervescent granulate according to the invention allows water-insoluble pesticidal active ingredients to be converted into a solid water- and solvent-free concentrate that disintegrates extraordinarily rapidly in water to form a sprayable suspension. It is especially advantageous that hydrophobic active ingredients can also be formulated as effervescent tablets that disintegrate rapidly in water to form a sprayable suspension. This was not possible with the methods hitherto known because of the fact that, in the small particle size necessary for the formation of a sprayable suspension, such hydrophobic active ingredients render inactive customary disintegrators consisting of sodium carbonate and a solid water-soluble acidic substance. A further advantage is that, with the present invention, very large effervescent tablets having a diameter of from 70 to 100 mm can also be prepared without difficulty, these tablets disintegrating in water in from 2 to 3 minutes despite their size. Such large effervescent tablets considerably facilitate the metering of the active ingredient, since the required amount of active ingredient for a spray tank is contained in a single effervescent tablet or in a small number of effervescent tablets.

The following Examples explain in greater detail the preparation of the effervescent granulate according to the invention and its use in the preparation of effervescent tablets.

EXAMPLE 1

Preparation of the effervescent granulate a) 3.459 kg of anhydrous citric acid and 3.459 kg of anhydrous potassium carbonate are mixed in powder form with 0.441 kg of Sipernat® 50S (highly dispersed silicic acid having a mean agglomerate size of 8 μm and a surface area according to BET of 450 m$^2$/g). The resulting powder mixture is stirred with 2.8 l of isopropanol to form a paste. The paste is then dried at 60° C. under a pressure of from 20 to 30 mbar for one hour in order to remove the isopropanol completely, and the residue is ground to a particle size of 0.8 mm. The resulting granulate can be used directly for the preparation of effervescent tablets without further treatment.

b) 4.70 kg of anhydrous adipic acid and 4.70 kg of anhydrous potassium carbonate are mixed in powder form with 0.60 kg of Sipernat® 50S (highly dispersed silicic acid having a mean agglomerate size of 8 μm and a surface area according to BET of 450 m$^2$/g). The resulting powder mixture is stirred with 2.7 l of isopropanol to form a paste. The paste is then dried at 60° C. under a pressure of from 20 to 30 mbar for one hour in order to remove the isopropanol completely, and the residue is ground to a particle size of 0.8 mm. The resulting mixture can be used directly for the preparation of effervescent tablets without further treatment.

c) 3.459 kg of anhydrous citric acid and 3.459 kg of anhydrous potassium carbonate are mixed in powder form with 0.441 kg of Sipernat® 50S (highly dispersed silicic acid having a mean agglomerate size of 8 μm and a surface area according to BET of 450 m$^2$/g). The resulting powder mixture is stirred with 2.8 l of isobutanol to form a paste. The paste is then dried at 60° C. under a pressure of from 20 to 30 mbar for one hour in order to remove the isobutanol completely, and the residue is ground to a particle size of 0.8 mm. The resulting granulate can be used directly for the preparation of effervescent tablets without further treatment.

EXAMPLE 2

Preparation of effervescent tablets 0.92 kg of 1-[2-(2,4-dichlorophenyl)-pentyl]-1H-1,2,4-triazole (penconazole) and 0.08 kg of Sipernat® 50S are mixed, and then ground to a mean particle size of from 8 to 10 μm in a jet mill. A powder is obtained which has good flow properties and exhibits no tendency to cake. For the preparation of a feedstock that is suitable for direct use in the formation of tablets, the finely ground active ingredient is mixed homogeneously with a homogeneous powder mixture of 0.981 kg of dispersing agent (condensation product of naphthalenesulfonic acid, phenolsulfonic acid and formaldehyde), 0.245 kg of sodium laurylsulfate, 0.184 kg of sodium benzoate, 0.061 kg of magnesium stearate, 2.435 kg of lactose (Tablettose® EP 6113) and 7.36 kg of the effervescent granulate prepared according to Example 1. In this manner there is obtained a feedstock having the following composition:

7.50% by weight of penconazole
4.25% by weight of Sipernat® 50S
8.00% by weight of dispersing agent
2.00% by weight of sodium laurylsulfate
1.50% by weight of sodium benzoate
0.50% by weight of magnesium stearate
28.20% by weight of citric acid
28.20% by weight of potassium carbonate
19.85% by weight of lactose.

The feedstock, which has good flow properties, is then compressed in a conventional tablet-forming device under a pressure of 600 kg/cm$^2$ to form tablets having a diameter of 76 mm, a thickness of 9 mm and a weight of 50 g. The tablets have good mechanical strength. The disintegration time in water is from 2 to 3 minutes. The resulting suspension is directly sprayable without further treatment.

What is claimed is:

1. An effervescent granulate having a mesh size of from 0.5 to 1 mm. which consists essentially of:
   a) water-soluble polybasic acid or an acid salt thereof;
   b) a carbonate selected from the group consisting of potassium carbonate and potassium hydrogen carbonate;
   c) a finely divided water-insoluble substance that binds water, selected from the group consisting of (1) a highly dispersed precipitated or pyrogenic silicic acid, (2) an amorphous aluminosilicate containing from 5 to 30% by weight of Al$_2$O$_3$ and from 70 to 95% by weight of SiO$_2$ and having an inner surface area, measured according to BET, of from 50 to 800 m$^2$/g, a pore volume of from 0.2 to 3 cm$^3$/g and a particle size of from 8 to 25 μm, (3) a natural or synthetic zeolite having a particle size of from 8 to 25 μm, and (4) aluminum oxide; and wherein the effervescent granulate has from 80 to 95% by weight of a) and b) combined and from 5 to 20% by weight of c), and the equivalent ratio of a) to b) is from 0.5 to 1.5.

2. An effervescent granulate according to claim 1, wherein the solid water-soluble acidic substance is a polybasic acid or an acid salt of a polybasic acid.

3. An effervescent granulate according to claim 2, wherein the solid water-soluble acidic substance is a polybasic carboxylic acid or an acid salt of a polybasic carboxylic acid.

4. An effervescent granulate according to claim 3, wherein the solid water-soluble acidic substance is succinic acid, tartaric acid, adipic acid, citric acid or an acid salt thereof.

5. An effervescent granulate according to claim 4, wherein the solid water-soluble acidic substance is citric acid or an acid salt of citric acid.

6. An effervescent granulate according to claim 1, which contains from 0.8 to 1.2 equivalents of a solid water-soluble acidic substance per equivalent of potassium carbonate and/or potassium hydrogen carbonate.

7. An effervescent granulate according to claim 6, which contains from 1.0 to 1.2 equivalents of a solid water-soluble acidic substance per equivalent of potassium carbonate and/or potassium hydrogen carbonate.

8. An effervescent granulate according to claim 1, wherein the highly dispersed silicic acid is precipitated or pyrogenic silicic acid.

9. An effervescent granulate according to claim 8, which contains precipitated or pyrogenic silicic acid having an agglomerate size of from 5 to 50 μm and a surface area, measured according to BET, of from 200 to 500 $m^2/g$.

10. An effervescent granulate according to claim 1, wherein the crystalline aluminosilicate is a natural or synthetic zeolite having a particle size of from 8 to 25 μm.

11. An effervescent granulate according to claim 1, which further contains an aluminium oxide.

12. An effervescent granulate according to claim 1, wherein the water-insoluble substance capable of binding water contains less than 5% by weight of water.

13. An effervescent granulate according to claim 12, wherein the water-insoluble substance capable of binding water contains less than 3% by weight of water.

14. An effervescent granulate according to claim 1, which contains from 5 to 10% by weight of a finely divided water-insoluble substance capable of binding water.

* * * * *